(12) United States Patent
Han et al.

(10) Patent No.: US 11,324,726 B2
(45) Date of Patent: May 10, 2022

(54) SMALL MOLECULAR STEMAZOLE FOR PROMOTING STEM CELL CLONAL FORMATION AND APPLICATIONS THEREOF

(71) Applicant: BEIJING NORMAL UNIVERSITY, Beijing (CN)

(72) Inventors: Mei Han, Beijing (CN); Jinhua Wen, Beijing (CN); Ying Sun, Beijing (CN); Huajun Li, Beijing (CN)

(73) Assignee: BEIJING NORMAL UNIVERSITY, Beijing (CN)

( * ) Notice: Subject to any disclaimer, the term of this patent is extended or adjusted under 35 U.S.C. 154(b) by 712 days.

(21) Appl. No.: 16/302,571

(22) PCT Filed: May 17, 2017

(86) PCT No.: PCT/CN2017/084650
§ 371 (c)(1),
(2) Date: Nov. 16, 2018

(87) PCT Pub. No.: WO2017/198164
PCT Pub. Date: Nov. 23, 2017

(65) Prior Publication Data
US 2019/0209533 A1    Jul. 11, 2019

(30) Foreign Application Priority Data

May 17, 2016 (CN) .......................... 201610325939.4

(51) Int. Cl.
| | |
|---|---|
| C07D 271/06 | (2006.01) |
| C07C 337/06 | (2006.01) |
| C12N 5/0735 | (2010.01) |
| C12N 5/0797 | (2010.01) |
| C12N 5/071 | (2010.01) |
| A61K 31/4245 | (2006.01) |

(52) U.S. Cl.
CPC ........ *A61K 31/4245* (2013.01); *C07C 337/06* (2013.01); *C07D 271/06* (2013.01); *C12N 5/0606* (2013.01); *C12N 5/0623* (2013.01); *C12N 5/0678* (2013.01); *C12N 2501/999* (2013.01)

(58) Field of Classification Search
None
See application file for complete search history.

(56) References Cited

FOREIGN PATENT DOCUMENTS

CN    101519385 A  *  9/2009

OTHER PUBLICATIONS

Sun et al., Eur J Med Chem. Jul. 2011;46(7):2930-2936 (Year: 2011).*
Corning® 384-well Flat Clear Bottom Black Polystyrene TC-treated Microplates; downloaded from ecatalog.corning.com on Nov. 16, 2021 (Year: 2021).*

* cited by examiner

*Primary Examiner* — Daniel C Gamett
(74) *Attorney, Agent, or Firm* — Lewis Roca Rothgerber Christie LLP

(57) ABSTRACT

Provided in the present invention are uses of a compound as represented by formula I in preparing a stem cell apoptosis antagonist. Also provided are uses of the compound as represented by formula I in preparing a medicament for preventing or treating cell apoptosis-related diseases, and a culturing method employing the compound as represented by formula I for stem cell culturing. The compound as represented by formula I is (I).

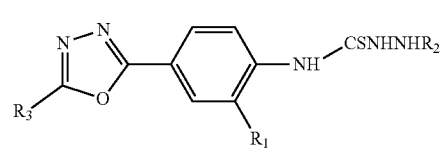

8 Claims, 6 Drawing Sheets

Figure 1
Fig. 1A
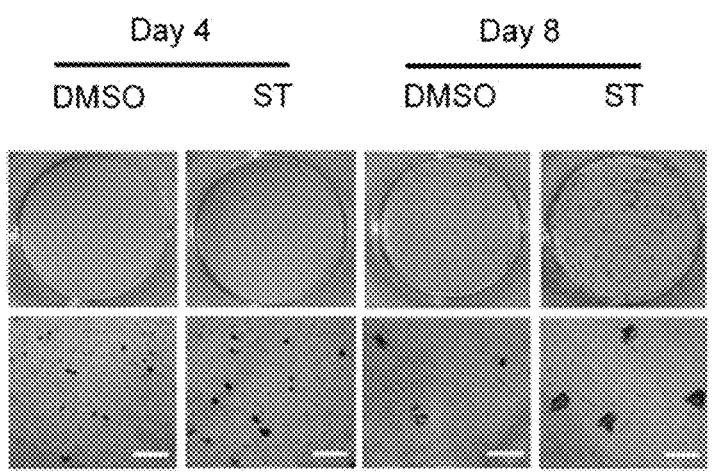
Fig. 1B
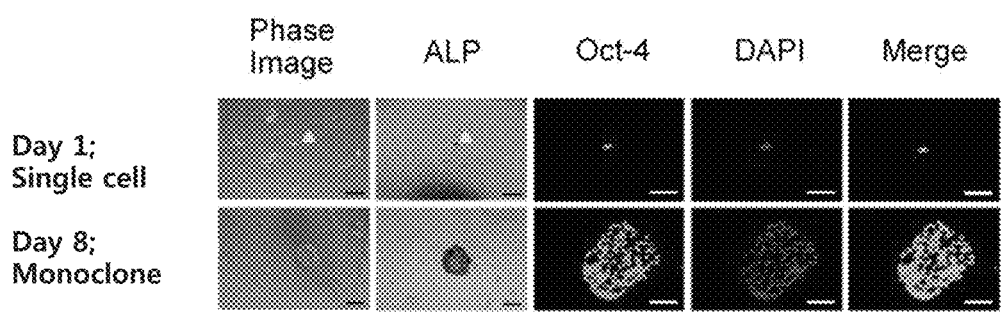

Figure 3
Fig. 3A
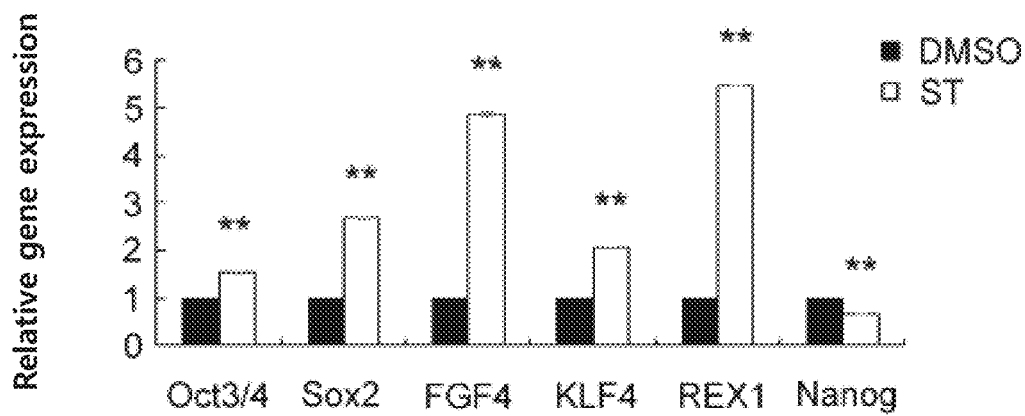
Fig. 3B
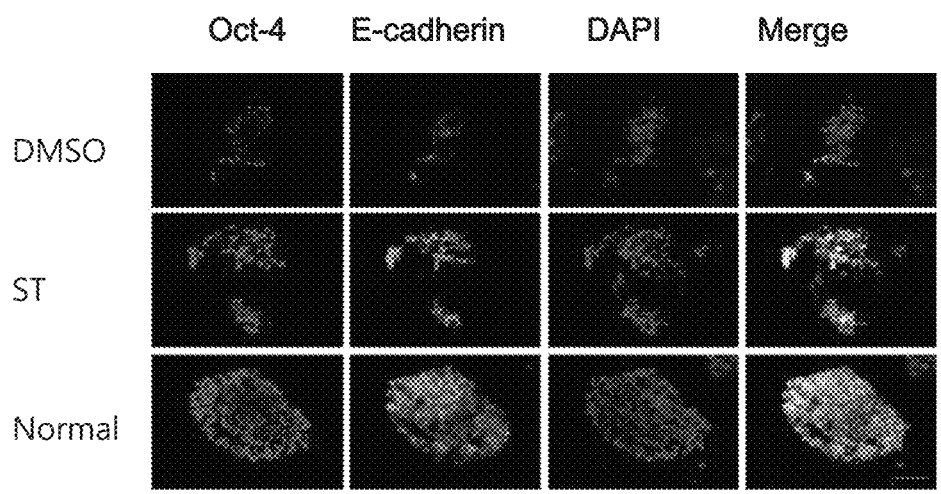

Figure 4
Fig. 4A
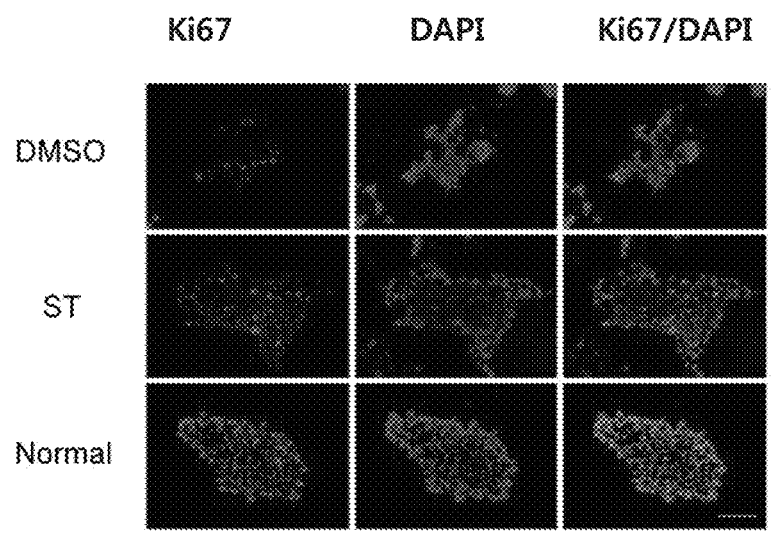
Fig. 4B
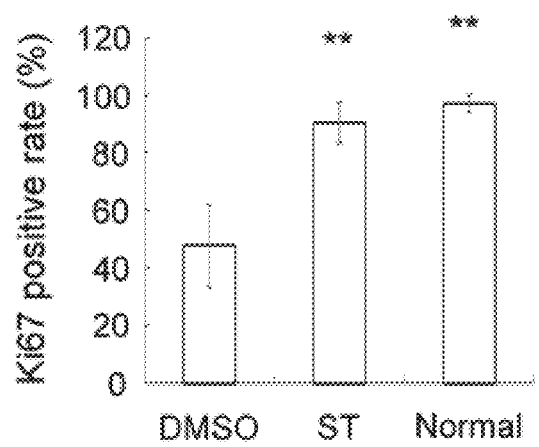

Figure 5
Fig. 5A
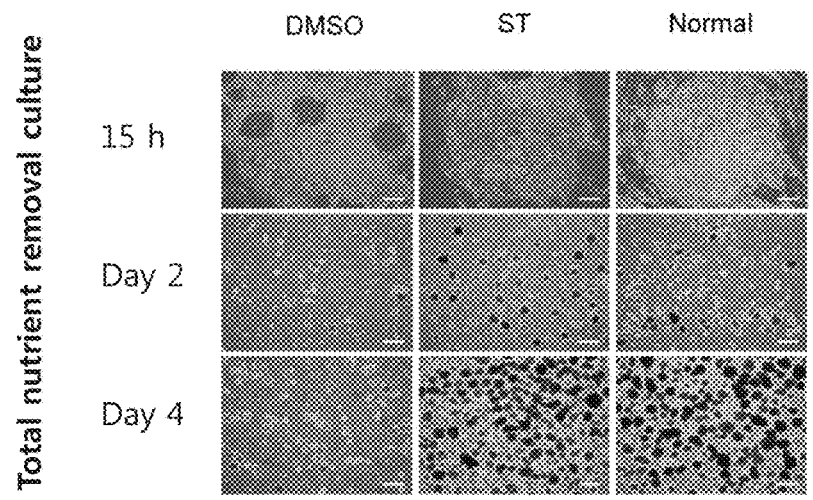
Fig. 5B
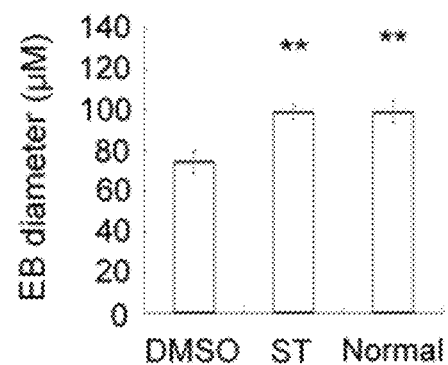
Fig 5C
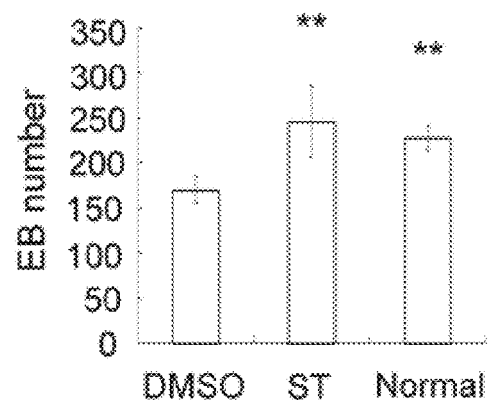

SMALL MOLECULAR STEMAZOLE FOR PROMOTING STEM CELL CLONAL FORMATION AND APPLICATIONS THEREOF

CROSS-REFERENCE TO RELATED APPLICATION(S)

This application is a U.S. National Phase Patent Application of International Application Number PCT/CN2017/084650, filed on May 17, 2017, which claims priority of Chinese Patent Application Number 201610325939.4, filed on May 17, 2016, the entire contents of all of which are incorporated herein by reference.

TECHNICAL FIELD

The present invention belongs to medical field Specifically, the present invention relates to the use of compound 4-(4-(5-mercapto-1,3,4-oxadiazole-2-yl)phenyl)thiosemicarbazide (herein named as "Stemazole") and structural analogues thereof for the anti-apoptosis in in vivo/in vitro research or application of stem cells.

BACKGROUND OF THE INVENTION

Stem cells are initial cells of self-renewing ability and multi-directional differentiation potential, which can proliferate and differentiate directionally into different functional cells under certain conditions. Therefore, stem cell related technology can explore deeply into life sciences, screen drugs for preventing and treating disease, and develop individualized precision medical treatments, etc., thereby having a very broad prospect.

Among stem cells, human stem cells (hSCs) have the potential to differentiate into a plurality of cell tissues of human body. The research on hSCs has an important theoretical significance as well as a great value in organ regeneration/repair and disease treatment. For a long term, scientists in the field of stem cell research have conducted extensive research on human pluripotent stem cells, aiming to develop clinical applications of the cells in diseases such as spinal cord injury, Parkinson's disease, burns, heart disease, diabetes, and arthritis.

Isolating and culturing stem cells, ensuring the survival of them, maintaining the self-replication characteristic of them, then further amplifying them to obtain a sufficient number of cells, are an important foundation of stem cell scientific research and clinical application. However, although the isolation and culture techniques of various stem cells have been developed in the field, it is well known that human stein cells, including human embryonic stem cells, human somatic stem cells, and human induced pluripotent stem cells, are very prone to apoptosis under the condition of stem cell culture in vitro or in the state of disease in vivo, especially under single cell in vitro culture condition, which makes it difficult to carry out relevant basic research or clinical application work. Moreover, most human stem cell cultures currently require the addition of exogenous nutrients such as serum or various cytokines. However, the introduction of such exogenous nutrients often introduces heterologous genes or proteins as well as viruses and other unknown pathogens. Exogenous nutrients per se may also act as allergens, negatively affecting practical application of pluripotent stem cells.

Therefore, there is an urgent need in the art to develop a new method for antagonizing the apoptosis of stem cells, particularly, develop a novel method capable of avoiding the apoptosis of stem cells under condition of single-cell culture as well as conditions where any exogenous serum or growth factor or protein are excluded.

SUMMARY OF THE INVENTION

In view of the above problems, an object of the present invention is to provide a small molecule compound which highly inhibits apoptosis of stem cells, particularly human stem cells.

The inventors of the present invention have found that, during the isolation and in vitro culture of stein cells, small molecular compounds have obvious advantages. Firstly, the small molecular compounds can construct a proliferating culture system with clear chemical composition, precisely regulate and control stem cell fate, and avoid the influence of exogenous gene or protein contamination caused by exogenous serum or growth factor with unknown ingredients in the micro-environment of stem cells. Secondly, small molecules can greatly increase the amount of harvested homogeneous stein cells. Thirdly, the time course during which small molecules act is reversible and easy to be regulated, which makes small molecules readily used as research tools for complex mechanisms. Finally, small molecules can regulate both endogenous stem cells and exogenous stem cells, which make they have the most potential to develop into stem cell drugs.

However, the screening of functional small molecules is a difficult and complicated task, and small molecules which have anti-apoptosis activity in stem cell culture are rarer. Currently, only ROCK inhibitor Y-27632 (4-[(1R)-1-aminoethyl]-N-(pyridine-4-yl)cyclohexane-1-carboxamide, which structure is shown below) can inhibit the apoptosis induced by isolation that happens during stem cell culture, and has been used in in vitro stem cell culture. However, Y-27632 has not been found yet to have the function that promotes the formation of single-cell clones, nor have an anti-apoptotic activity in total nutrient removal culture.

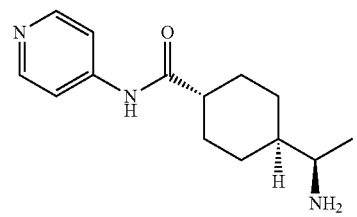 [SMILES: C[C@@H](N)[C@H]1CC[C@H](C(=O)Nc2ccncc2)CC1]

The inventors of the present invention, after a tremendous amount of research, have found that compound 4-(4-(5-mercapto-1,3,4-oxadiazole-2-yl)phenyl)thiosemicarbazide (herein named as "Stemazole") and structural analogues thereof can effectively inhibit apoptosis during single-cell culture and/or total nutrient removal culture of stein cells, especially human embryonic stem cells, as well as human somatic stein cells and compound Stemazole, without affecting the potential of stem cells per se in terms of self-replication and multi-directional differentiation, has a remarkable effect of antagonizing apoptosis of stem cells, and improves survival rate and clone formation efficiency of stem cells.

On the basis of the above, the present invention now provides following technical solutions.

In one aspect, the present invention provides use of a compound as represented by formula I in the manufacture of an apoptosis antagonist of stem cells:

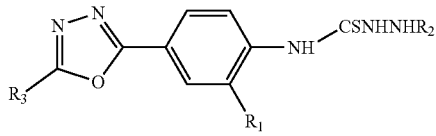

wherein $R_1$ is H, halogen, $C_1$-$C_4$ alkyl or $C_1$-$C_4$ alkoxy; $R_2$ is H, or $C_1$-$C_4$ alkyl; $R_3$ is H, halogen, sulfhydryl, hydroxy, $C_1$-$C_4$ alkyl, or heteroalkyl in which the heteroatom is oxygen or sulfur.

Preferably, when $R_1$ is halogen, it is Br.

Preferably, the heteroalkyl is $C_1$-$C_4$ alkyl substituted by oxygen or sulfur.

Preferably, the present invention provides use of compound 4-(4-(5-mercapto-1,3,4-oxadiazole-2-yl)phenyl)thiosemicarbazide in the manufacture of an apoptosis antagonist of stem cells.

The structure of compound 4-(4-(5-mercapto-1,3,4-oxadiazole-2-yl)phenyl)thiosemicarbazide is represented by following formula Ia:

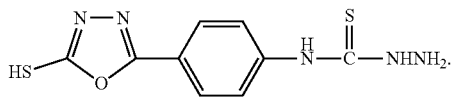

The compound as represented by formula Ia is named as "Stemazole" herein, which can be synthesized according to the steps and route as described in Example 1 of Chinese patent publication CN101519385A.

The present invention also provides use of compound 4-(2-br-4-(5-mercapto-1,3,4-oxadiazole-2-yl)phenyl)thiosemicarbazide in the manufacture of an apoptosis antagonist of stem cells.

The structure of compound 4-(2-br-4-(5-mercapto-1,3,4-oxadiazole-2-yl)phenyl)thiosemicarbazide is represented by following formula Ib:

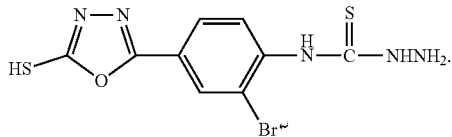

The compound as represented by formula Ib is named as "Br-Stemazole" herein.

As used herein, the term "apoptosis antagonist" refers to an agent that can inhibit apoptosis caused by various factors in vivo/in vitro, including apoptosis caused by culture in vitro or caused by various disease factors in vivo.

Preferably, the stem cells are human stem cells.

More preferably, the stem cells are human embryonic stem cells, human somatic stein cells or induced pluripotent stem cells. According to particular embodiments of the present invention, the stem cells are human embryonic stem cells, especially human embryonic stem cell strain H9, or human somatic stem cells, especially human somatic neural stem cells and/or human somatic pancreatic stem cells.

According to the research, the compound as represented by formula I can be used in in vitro single-cell culture of the stem cells to significantly inhibit apoptosis of the stem cells induced by isolation and culture, and to promote the formation of single-cell clones of the stem cells. The research also shows that the compound as represented by formula I can be used in in vitro total nutrient removal culture of the stem cells to significantly inhibit apoptosis of the stem cells in the absence of nutrients such as serum, growth factor, etc. essential to the in vitro culture.

Therefore, preferably, the apoptosis antagonist is used in the in vitro single-cell culture and/or in vitro total nutrient removal culture of the stein cells.

As described herein, the expression "in vitro single-cell culture" refers to in vitro single cell clone culture or low density cell culture, in which cell concentration is 1-100 cells/0.1 mL or 10-10; cells/mL.

As described herein, the expression "in vitro total nutrient removal culture" refers to culture under the condition of removing serum and growth factor from culture medium.

According to particular embodiments of the present invention, in vitro single-cell culture is culture performed by digesting the stem cells into single cell clones and inoculating into a corresponding culture system, for example, inoculating on low density feeder layer cells in corresponding culture medium.

According to particular embodiments of the present invention, the in vitro total nutrient removal culture refers to stem cell culture performed under the condition of removing serum and growth factor from culture medium.

In another aspect, the present invention further provides use of a compound as represented by formula I in the manufacture of a medicament for the prevention or treatment of an apoptosis-related disease.

As described herein, the expression "apoptosis-related disease" refers to apoptotic damage of various functional cells in vivo due to various pathogenic factors.

Since the compound as represented by formula I has the above functions and characteristics, it can be used as an additive for in vitro culture of stem cells, especially human stem cells such as human embryonic stem cells or human somatic stein cells, in order to avoid apoptosis of a large amount of the stem cells during culture and promote the formation of single cell clones; or, to avoid the addition of exogenous serum, cytokines or proteins during in vitro culture, and to improve survival rate and clone formation efficiency of stein cells, without affecting the self-replication and multi-directional differentiation potential of stein cells per se.

Accordingly, in still another aspect, the present invention provides a method of culturing stein cells, including: performing in vitro single-cell culture and/or in vitro total nutrient removal culture of stem cells in the presence of a compound as represented by formula I.

Preferably, the stem cells are human stem cells.

More preferably, the stem cells are human embryonic stem cells, human somatic stem cells or induced pluripotent stem cells. According to particular embodiments of the present invention, the stem cells are human embryonic stem cells, especially human embryonic stem cell strain H9; or human somatic stem cells, especially human somatic neural stem cells and/or human somatic pancreatic stem cells.

Specifically, the above culture method provided by the present invention includes: adding the compound as represented by formula I into culture system of the in vitro single-cell culture and/or in vitro total nutrient removal culture of the stem cells. The culture system is a single-cell culture system or total nutrient removal culture system of the stem cells. In either system or in a combination of the two, the apoptosis of the stem cells will be significantly reduced in the presence of compound as represented by formula I. The compound as represented by formula I is present in the culture system at a concentration of 0.01-500 μM, preferably 1-150 μM.

As known in the art, when separated from in vivo microenvironment or existing in a destroyed microenvironment, most human stem cells including human embryonic stem cells, human somatic stem cells, and human induced pluripotent stem cells are very prone to apoptosis under in vitro single-cell culture conditions, which made related basic research or clinical application difficult to carry out. In addition, exogenous nutrients added during the culture also bring a negative impact on the development of stem cell applications. Therefore, inhibiting the apoptosis of stein cells, especially inhibiting the apoptosis of stem cells and promoting the survival, replication and proliferation of stem cells under the condition of removal of any exogenous serum or growth factor (or protein) by using small molecule compounds, has important scientific significance and broad application value.

The present invention demonstrates that the compounds as represented by formula I are a novel class of small molecule apoptosis antagonists of stem cells with stein cell regulatory activities: they can promote in vitro clone formation of individual stem cells and inhibit severe apoptosis which always occurs in low-density culture of stem cell in vitro, thus can effectively inhibit the apoptosis of stem cells induced by isolation and culture; besides, they can also inhibit severe apoptosis of stem cells caused by removal of total nutrients. Moreover, the compounds improve survival rate and clone formation rate of embryonic stem cells without affecting the self-renewal or pluripotency characteristics of stem cells. Therefore, the compounds as represented by formula I, as protective agents and apoptosis antagonists of stem cells, have marvelous potentials in being developed into additives for in vitro culture which can effectively inhibit stem cell apoptosis and maintain stemness of the cells. For example, they can be widely used in in vitro culture of stem cells, especially in vitro culture of human stem cells, such as human embryonic stem cells or human somatic stem cells, helping to solve the technical problem of apoptosis highly prone to occur during cell isolation and culture; they can also eliminate the contamination and effects of exogenous genes and/or proteins on stem cell growth by replacing current used sera and/or growth factors which comprise uncertain ingredients or foreign genes, thus building a foundation for stem cell basic researches and clinical applications in future.

In addition, the compounds as represented by formula I, as small molecule compounds, have many advantages in cell separation, culture, and convenience for regulation etc. In particular, the compounds as represented by formula I are compared with the currently known apoptosis antagonist Y-27632 in the present invention and, it has found that the compounds as represented by formula I can achieve an anti-apoptotic effect comparable to the ROCK inhibitor Y-27632, therefore, can also be developed into commercialized, brand new in vitro culture additives for stem cells, promoting in vitro stem cell survival, antigonizing apoptosis, and helping to maintain stem cell characteristics.

BRIEF DESCRIPTION OF THE DRAWINGS

Hereinafter, the embodiments of the present invention will be described in detail with reference to the accompanying drawings, in which:

FIG. 1 shows the staining results of the cells in the experiment group and the control group in Example 1, in which FIG. 1A shows the results of alkaline phosphatase staining of the experiment group (ST) and the control group (DMSO) on day 4 and day 8, and FIG. 1B shows the results of the OCT-4 immunofluorescence staining of the experiment group (ST) on day 1 and day 8.

FIG. 3 shows the expression of important markers of human embryonic stem cells in Example 5, in which FIG. 3A shows the detection by quantitative PCR and FIG. 3B shows the detection by immunofluorescence staining.

FIG. 4 shows the expression of proliferation markers of human embryonic stem cell in Example 5, in which FIG. 4A shows the results of immunofluorescence staining and FIG. 4B shows the positive rate of expression of proliferation markers.

FIG. 5 shows the differentiation ability to form embryoid bodies (EBs) in Example 5, in which FIG. 5A is a microscopic image of each group at different time and FIGS. 5B and 5C show the diameters and number of the formed EBs, respectively.

DETAILED DESCRIPTION OF PREFERRED EMBODIMENTS

Figure 2:
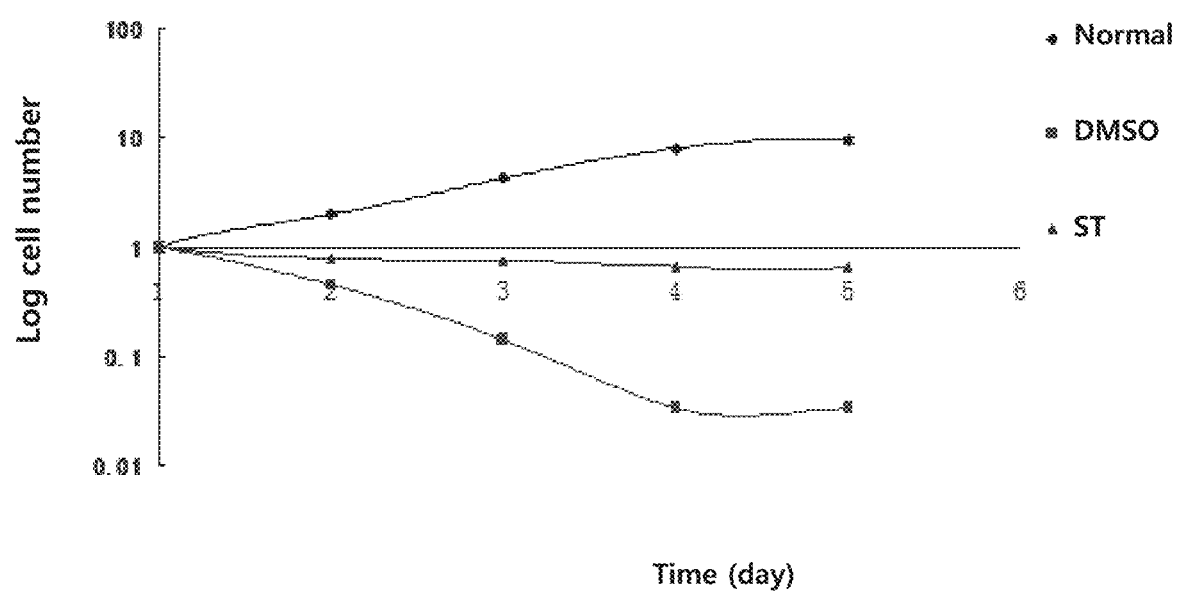
FIG. 2 shows the changes in the number of cells in the three groups in Example 4 as a function of culture time.

The present invention is described below with reference to particular Examples. Those skilled in the art can understand that the Examples are only used to illustrate the invention and are not intended to limit the scope of the invention in any way.

Pharmaceutical materials, reagent materials and the like used in the following Examples are commercially available products, unless particularly stated. Some of the materials are purchased as follows:

Human embryonic stein cell strain H9 is purchased from Peking University Stem Cell Center.

Specific apoptosis detection kit Annexin V/PI is purchased from Beyotime Biotechnology, China.

Experimental methods in the following Examples are conventional methods, unless particularly stated. Some of the experimental methods are as follows:

Alkaline Phosphatase Staining—
1) Rinsing cells with PBS, 3 times;
2) Fixing the cell with 4% paraformaldehyde for 10 minutes;
3) Washing with PBS, 3 times;
4) Preparing alkaline phosphatase staining agent:solution A:solution B:solution C=10 μl:10 μl:1 ml;
5) Adding the alkaline phosphatase staining agent to cover the cells, and staining for 20 minutes at room temperature in dark;
6) Aspirating off the staining agent, rinsing with PBS 3 times, storing the cells in PBS, and observing staining under a microscope.

Immunofluorescence Staining—
1) Washing processed slide with cells thereon with 1×PBS 3 times, 5 minutes for each time;

2) permeabilizing the cells with PBS containing 0.5% Triton X-100 at room temperature for 15 minutes;
3) Washing with PBS 3 times, 5 minutes for each time;
4) Blocking with 5% sheep serum at 37° C. for 30 minutes;
5) Adding primary antibody and incubating at room temperature for 3-4 hours, or at 4° C. overnight;
6) Washing with PBS 3 times, 5 minutes for each time;
7) Adding fluorescent-labeled secondary antibody, and incubating at 37° C. for 1 hour;
8) Washing with PBS 3 times, 5 minutes for each time;
9) Mounting the slide with mounting agent containing DAPI;
10) Observing under a fluorescence microscope or confocal microscope, and taking photos.

Complete culture medium used in the following Examples is:

Basic medium DMEM/F12, supplemented with 20% serum substitute, 2 mM glutamine, 0.1 mM 3-thioethanol, 0.01 mM non-essential amino acid, 100 units/ml penicillin, 100 units/ml streptomycin, and 10 ng/ml growth factor bFGF.

Example 1 Stemazole Promotes the Formation of Single Cell Clones in Single-Cell Culture of Human Embryonic Stem Cells After being digested into single cells, human embryonic stem cell strain H9 cells were divided into two groups as follows, and inoculated on low density MEF feeder layer cells in 96-well plates:

Experiment group (ST group): complete medium+Stemazole dissolved in DMSO at a final concentration in the culture medium of 100 μM;

Control group (DMSO group): complete medium+DMSO with an amount corresponding to the experiment group.

The cell ratio of each well in the two groups was H9 cell/100 MEF cells, and the medium was supplemented once every 4 days.

Alkaline phosphatase staining was performed on day 4 and day 8. The results are shown in FIG. 1A: the number and sizes of the clones formed by the H9 cells in the DMSO group were less and smaller, while the number and sizes of the clones formed in ST group were higher and larger. Statistical analysis of the number of cell clones in the two groups showed that the number of clones of alkaline phosphatase positive cells in the DMSO group averaged about 8 on day 4, and the number of clones of the alkaline phosphatase positive cells in the ST group averaged about 18, and the difference between the numbers of clones in the two groups was significant. The number of clones of alkaline phosphatase positive cells in the DMSO group averaged about 12 on day 8, and the number of clones of the alkaline phosphatase positive cells in the ST group averaged about 23, and the difference between the number of the clones in the two groups was significant. As to the size, the diameter of the alkaline phosphatase positive cells in the DMSO group on day 4 averaged about 50 microns, and the diameter of the alkaline phosphatase positive cells in the ST group averaged about 100 microns. There was no significant difference between the sizes of the clones in the two groups. The diameter of the alkaline phosphatase positive cells in the DMSO group on day 8 averaged about 70 microns, and the diameter of the alkaline phosphatase positive cells in the ST group averaged about 200 microns. There was a significant difference between the sizes of the clones in the two groups.

OCT-4 immunofluorescence staining was performed on day 1 and day 8. The results are shown in FIG. 1B: in the ST group, single 1-19 cells were observed growing by adhering to the wall, which revealed that H1-9 single cells had grown into monoclonal cells; and in the DMSO group, no single 1-19 cells were observed adherent to the wall, neither 1-19 monoclonal cells were found.

Example 2 Stemazole Reduces Apoptosis in Human Embryonic Stem Cell Single-Cell Culture Human embryonic stem cell line H9 cells were digested into single cells, divided into 3 groups as follows, and then inoculated at a low density on low-density MEF feeder layer cells in 6-well plates:

Experiment group (ST group): complete medium+Stemazole dissolved in DMSO at a concentration in the final culture medium of 100 μM;

Negative control group (DMSO group): complete medium+DMSO at an amount corresponding to the experiment group;

Positive control group (Y27632 group): complete medium+Y27632 dissolved in DMSO at a concentration in the final culture medium of 10 μM.

The cell ratio of each well of the three groups was 10 H9 cells/1 MEF cell.

Apoptosis was detected by flow cytometry using the specific apoptosis assay kit Annexin V/PI on day 2 of inoculation.

The results showed that: the DMSO group had the largest number of Annexin V positive apoptotic cells, which accounted for 54.1% in average; apoptotic cells in the ST group were obviously less than that in the DMSO group, and accounted for 25.2% in average; and the apoptotic cells in the Y27632 group was the least, and accounted for 20.1% in average. Statistical analysis showed that there was a significant difference between the DMSO group and the ST group as well as between the DMSO group and the Y27632 group, but there was no significant difference between the ST group and the Y27632 group.

The small molecule compound Stemazole of the present invention has a completely different chemical structure from that of the ROCK inhibitor Y-27632, but achieves a comparable inhibitory effect on apoptosis. Thus it can be used as a new antagonist of apoptosis of stem cells.

Example 3 Stemazole Reduces Apoptosis of Human Embryonic Stem Cells During Total Nutrient Removal Culture After passaged, human embryonic stem cell line H9 cells were divided into the following two groups and inoculated in 6-well plates:

Experiment group (ST group): total nutrient removal culture medium (complete medium with removal of serum and growth factor)+Stemazole dissolved in DMSO at a final concentration in the culture medium of 100 μM;

Control group (DMSO group): total nutrient removal culture medium+DMSO with an amount corresponding to the experiment group;

Normal culture group: complete medium.

Apoptosis was detected by flow cytometry using the specific apoptosis assay kit Annexin V/PI.

The results showed that: the percent apoptotic cells in the normal culture group was about 0.4%; while, under the condition of any exogenous serum or growth factor being removed (i.e., under the condition of total nutrient removal or nutrient starving) for 15 hours, early apoptosis occurred in the DMSO group, and the apoptosis rate was about 43%. In contrast, there was no significant apoptosis in the ST group, in which the apoptosis rate was about 8%. Compared to the DMSO group, an obvious anti-apoptotic performance was found in the ST group.

Example 4 Stemazole Reduces Apoptosis Rather than Promotes Proliferation in Single-Cell Culture of Human Embryonic Stem Cells Human embryonic stem cell strain H1-9 cells were digested into single cells, then divided into following three groups and inoculated on low-density MEF feeder layer cells in 6-well plates:
Experiment group (ST group): complete medium+Stemazole dissolved in DMSO at a final concentration in the culture medium of 100 μM;
Control group (DMSO group): complete medium+DMSO with the amount corresponding to the experiment group;
Normal culture group: complete medium.
The cells in each well of the three groups were maintained well grown on the MEF feeder layer cells, and the medium was supplemented once every 4 days.
The number of cells in the three groups was measured as a function of time, and the results are shown in FIG. 2: the number of the cells in the ST experiment group did not increase, and after a slight decrease, remained constant as time passed. The results of this experiment prove that the biological effect of ST is to maintain cell survival, and ST does not show its activity to promote proliferation of the H9 cell line.

Example 5 Stemazole Maintains the Stemness of Human Embryonic Stem Cells

I. Expression of Important Marker Proteins of Human Embryonic Stem Cells

Following the experimental method in Example 3, H9 cells were divided into experiment group (ST group) and control group (DMSO group) and cultured. After 15 hours of total nutrient removal culture, the expression of each of human embryonic stem cells' important markers OCT-4, Sox2, FDF4, KLF4, REX1, and Nanog was detected by quantitative PCR.

1. Quantitative PCR reaction system:

| Agent | Volume |
| --- | --- |
| 2X SYBR Green Mix | 7.5 μl |
| Upstream primer | 0.5 μl |
| Downstream primer | 0.5 μl |
| cDNA template | 1 μl |
| Sterile water | 5.5 μl |

2. Reaction conditions of quantitative PCR:

| Step | Setting |
| --- | --- |
| Stage I | 95° C., 5 min |
| Stage II | 95° C., 15 s; 60° C., 1 min; 40 cycles |
| Stage III | 95° C., 15 s; 60° C., 1 min; 95° C., 30 s; 1 cycle |

3. Data Analysis:

Ct (Cycle threshold) of each sample was measured by calculating $2^{-\Delta\Delta Ct}$, to compare differential expression of specific gene between different samples. In order to reduce systematic error and sampling error, triplicate wells in parallel were set for each sample. The average value of the triplicate wells was taken as the Ct of the sample, and then $2^{-\Delta\Delta Ct}$ was calculated according to the formulas below. Each experiment was repeated at least 3 times, and the results are shown in a column chart in form of average value±standard deviation.

$$\Delta Ct_{experiment\ group} = Ct_{gene\ in\ experiment\ group} - Ct_{reference\ gene\ in\ experiment\ group}$$

$$\Delta\Delta Ct_{control\ group} = Ct_{gene\ in\ control\ group} - Ct_{reference\ gene\ in\ control\ group}$$

$$\Delta\Delta Ct = \Delta Ct_{experiment\ group} - \Delta Ct_{control\ group}$$

$$2^{-\Delta\Delta Ct} = 2^{-(\Delta Ct experiment\ group - \Delta Ct control\ group)}$$

The results are shown in FIG. 3A. It was found that after being subjected to the nutrient starving culture, the H9 cells still expressed important markers OCT-4, Sox2, FDF4, KLF4, REX1, and Nanog of stem cells, i.e., Stemazole maintained the stem cell characteristics of the 1-19 cells under the condition of total nutrient removal culture.

In addition, still following the experimental method in Example 3, 1H9 cells were divided into experiment group (ST group), control group (DMSO group) and normal culture group and cultured. After total nutrient removal culture for 15 hours, the expression of each of human embryonic stem cells' important markers OCT-4 and E-Cadherin was detected by immunofluorescence staining.

The results are shown in FIG. 3B. It was found that after being subjected to the nutrient starving culture, the H9 cells still expressed important markers OCT-4 and E-Cadherin of stem cells, i.e., Stemazole maintained the stem cell characteristics of 1-19 cells under the condition of total nutrient removal culture.

II. Detection of Proliferation Marker of Human Embryonic Stem Cells

Following the experimental method in Example 3, H9 cells were divided into experiment group (ST group), control group (DMSO group) and normal culture group and cultured. After total nutrient removal culture for 15 hours, immunofluorescence staining of the H9 cells was conducted for Ki67 (a proliferation marker).

The results are shown in FIG. 4A and FIG. 4B. It was found that the H9 cells still highly expressed Ki67, i.e., Stemazole maintained the proliferation ability of the H9 cells.

III. Detection of Differentiation Potential for Forming Embryoid Bodies

Following the experimental method in Example 3, H9 cells were divided into experiment group (ST group), control group (DMSO group) and normal culture group and cultured. The formation of EBs was observed under a microscope at the 15th hour, and on day 2 and day 4 of total nutrient removal culture respectively, and the diameter and number of EBs were measured at the 15th hours.

The results are shown in FIGS. 5A, 5B and 5C. It was found that EBs could still be formed from the H9 cells, i.e., Stemazole maintained the multi-directional differentiation potential of the H9 cells. And compared to the unprotected DMSO group, more EBs with larger diameter were formed in the ST group which was protected by Stemazole, and there was a significant difference between the two groups.

IV. Detection of Ability of Induced Differentiation into Endoderm, Mesoderm and Ectoderm Cells Following the experimental method in Example 3, H9 cells were divided into experiment group (ST group), control group (DMSO group) and normal culture group and cultured.

The H9 cells were digested by Collagenase IV, washed with DMEM (high glucose) 3 times, and gently blown into small cell clusters, then were inoculated into 100 mm petri dishes with the culture medium changed into differentiation culture medium (DMEM/F12, 20% FBS, 1× non-essential amino acid, 1×sodium pyruvate, 1×β-mercaptoethanol, double antibiotics, and 2 mM glutamine). The medium was changed every 2 days, and the dishes were observed on each day. After 4 days, RNA was extracted and the differentiation ability of the H9 cells to endoderm, mesoderm and ectoderm cells was detected.

The results showed that the EBs formed from the cells in the three groups multi-directionally differentiated. The expression of CK8 and CK18 of endoderm; Brachyury and MSX1 of mesoderm; and GFAP, Pax6, and MAP2 of ectoderm were all detected. In terms of the expression of mesoderm marker MSX1, the expression of the DMSO group and the expression of the ST group (both groups were subjected to nutrient starving for 15 hours) were higher than that of normal control group cells which did not experience nutrient starving, and the expression of the DMSO group was comparable to that of the ST group. In terms of expression of ectoderm marker GFAP, the expression of the DMSO group which was subjected to nutrient starving for 15 hours was less than that of the ST group, and the expression of the ST group was comparable to that of the normal control group cells which did not experience nutrient starving. In terms of expression of ectoderm marker Pax6, the expression of the DMSO group was comparable to that of the ST group, while both higher than that of normal control group cells which did not experience nutrient starving. There was no significant difference found in the expression of other individual markers. All experiments had been repeated 3 times to confirm the results.

Example 6 Stemazole and Br-Stemazole Improve Cell Viability of Human Hippocampal Neurosphere Stem Cells 1. Culture of Human Hippocampal Neurosphere Stem Cells 1) On a superclean bench and under sterile conditions, human embryo hippocampus was taken out;

2) After envelope and blood vessels were removed under a dissecting microscope, tissue obtained was rinsed with pre-cooled PBS at 4° C. 3-5 times, leaving a very small amount of PBS;

3) The tissue was cut into pieces using ophthalmic scissors, and about 5 ml of culture medium was added to suspend the tissue pieces, and then the obtained cell suspension was gently pipetted to achieve single cell state with a pipette tip;

4) The cell suspension was filtered through a 40 μm pore size cell sieve;

5) Cell density was regulated to $1\times10^6$/ml, and then the cells were inoculated into a 75 cm$^3$ glass culture flask;

6) The cells in the flask were cultured in a 37° C., 5% $CO_2$ cell culture incubator.

2. Cell Viability Assay

Figure 6:
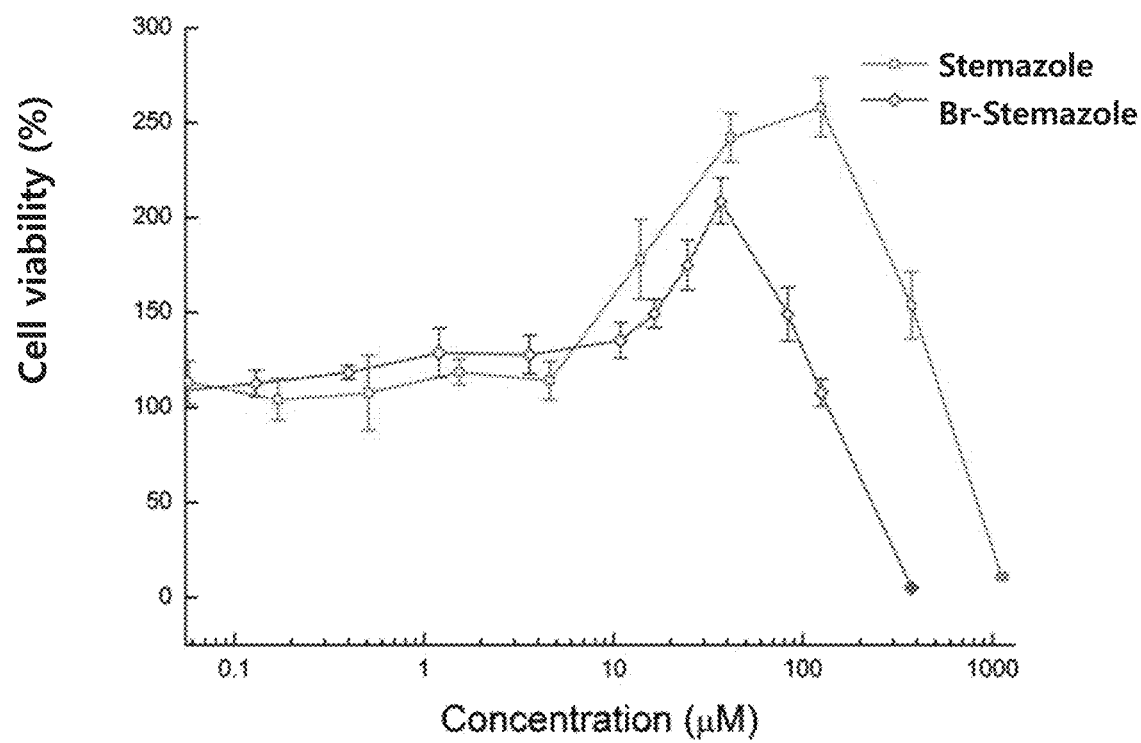
FIG. 6 shows the cell viability of human hippocampal neurosphere stem cells in the presence of Stemazole and Br-Stemazole in Example 6.

The human hippocampal neurosphere stem cells were mechanically pipetted into small clones, regulated into a suitable density, and inoculated into a 96-well, black-wall plate at about 50 neurospheres/110 μL cell suspension/well. Solvent DMSO was used as control, and series concentrations of compound preparations were added respectively at 10 μL/well, in which the compound was Stemazole or Br-Stemazole, thereby obtaining concentrations of the compound in the cell suspensions as shown in FIG. 6; then the plate was cultured in a 37° C., 5% $CO_2$ cell culture incubator. Without changing the medium, ATP was added at 20 μL/well after the compound acted for 4 days or other time, and the viability of cells was detected.

The results are shown in FIG. 6. It was found that on screening platform of human neurosphere stem cells derived from hippocampus, both compound Stemazole and Br-Stemazole had a protective effect on the cell viability of human hippocampal neurosphere stem cells, in a dose-effect relationship. Compared with Br-Stemazole, the biological activity of Stemazole was stronger, and the cell viability increased up to 2.7 times over the control group; while Br-Stemazole also was found to have a biological activity, and the cell viability increased up to 2.1 times over the control group.

Human SSP neural precursor cells and human embryonic pancreatic precursor cells were also used for performing the experiment, and the same results were obtained.

In summary, the present application has demonstrated that the application of the compounds of formula I to in vitro single-cell culture of stem cells can significantly promote the formation of single cell clones of stem cells, and can also significantly inhibit apoptosis of stein cells in low concentration culture. Therefore, the compounds can help to solve technical problems in cell isolation and culture. Moreover, the compounds of formula I can be used for in vitro total nutrient removal culture of stem cells, during which they can significantly inhibit apoptosis of the stem cells in the absence of nutrients such as serum, growth factor and the like essential to in vitro culture, thereby excluding the contamination and influence of exogenous genes or proteins on stem cell growth, which is more beneficial to basic research and clinical application of stem cells. In particular, the use of the compounds of formula I also maintains the characteristics, proliferative capacity and multi-directional differentiation potential of stem cells, because the compounds exert their anti-apoptotic effect without sacrificing stem cell characteristics.

In addition, the compounds of formula I can also be used for somatic stem cells and can increase the cell viability of human somatic stem cells such as human hippocampal neurosphere stem cells, human SSP neural precursor cells, human pancreatic precursor cells and the like.

In conclusion, the compounds of formula I can be widely applied to in vitro culture of human cells, especially human embryonic stem cells or human somatic stem cells, and lay a foundation for further deeper research.

The above description of the specific embodiments of the present invention is not intended to limit the invention, and various modifications and changes may be made by those skilled in the art without departing from the spirit and scope of the invention, and belong to the scope of the following claims of the invention.

What is claimed is:

1. A method of culturing stem cells, including: performing in vitro single-cell culture in the presence of a compound as represented by formula I:

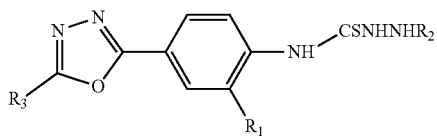

wherein in formula I, $R_1$ is H, halogen, $C_1$-$C_4$ alkyl or $C_1$-$C_4$ alkoxyl; $R_2$ is H, or $C_1$-$C_4$ alkyl; $R_3$ is H, halogen, sulfhydryl, hydroxy, or $C_1$-$C_4$ alkyl, or heteroalkyl in which a heteroatom is oxygen or sulfur, and characterized in that, a cell concentration of the in vitro single-cell culture is 1-100 cells/0.1 mL or 10-$10^3$ cells/mL.

2. The method according to claim 1, characterized in that, the stem cells are human stem cells.

3. The method according to claim 1, characterized in that, the method includes: adding the compound as represented by formula I into culture system of the in vitro single-cell culture, wherein
  a concentration of the compound as represented by formula I in the culture system is 1-100 μM.

4. The method according to claim 1, characterized in that, $R_1$ is Br.

5. The method according to claim 1, characterized in that, the heteroalkyl is C1-C4 alkyl substituted by oxygen or sulfur.

6. The method according to claim 1, characterized in that, the compound as represented by formula I is compound 4-(4-(5-mercapto-1,3,4-oxadiazole-2-yl)phenyl)thiosemicarbazide as represented by formula Ia:

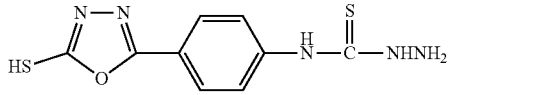

or,
the compound as represented by formula I is compound 4-(2-Br-4-(5-mercapto-1,3,4-oxadiazole-2-yl)phenyl) thiosemicarbazide as represented by formula Ib:

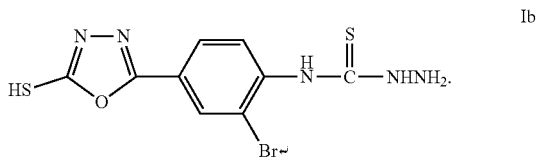 [SMILES: NNC(=S)Nc1ccc(-c2nnc(S)o2)cc1Br]

7. The method according to claim 1, characterized in that, the stein cells are human embryonic stein cells, human somatic stein cells or induced pluripotent stein cells.

8. The method according to claim 1, characterized in that, the stein cells are human embryonic stein cell strain H9, human somatic neural stein cells and/or human somatic pancreatic stem cells.

* * * * *